United States Patent [19]
Welsh et al.

[11] Patent Number: 5,892,018
[45] Date of Patent: Apr. 6, 1999

[54] DNA SEQUENCES ENCODING A BRAIN SODIUM CHANNEL PROTEIN

[76] Inventors: Michael J. Welsh, 3460 560th St., Riverside, Iowa 52327; Margaret P. Price, 605 Whiting Ave., Iowa City, Iowa 52246

[21] Appl. No.: 828,596

[22] Filed: Mar. 31, 1997

Related U.S. Application Data

[60] Provisional application No. 60/072,104 Apr. 2, 1996.
[51] Int. Cl.⁶ .......................... C12N 15/12; C12N 15/63; G07K 14/705
[52] U.S. Cl. .................... 536/23.5; 435/320.1; 435/69.1; 530/350
[58] Field of Search ................................ 435/69.1, 320.1, 435/325; 536/23.5; 530/380

[56] References Cited

PUBLICATIONS

Waldmann, et al. J. Biol. Chem. vol. 271(18): pp. 10433–10436, May 1996.
Price et al. J. Biol. Chem. vol. 271(14): pp. 7879–7882, Apr. 1996.
Kriegler, M. in Gene Transfer and Expression: A Laboratory Manual, pp. 3–176, Stockton Press, NY, New York, 1990.

*Primary Examiner*—Stephen Walsh
*Assistant Examiner*—Daryl A. Basham
*Attorney, Agent, or Firm*—Zarley, McKee, Thomte, Voorhees & Sease

[57] ABSTRACT

The present invention discloses a novel subfamily of amiloride sensitive sodium channel proteins isolated and purified from the human central nervous system. DNA sequences encoding such proteins are disclosed as are methods and procedures for development of pharmacologic agents for treatment of diseases associated with central nervous system dysfunction.

12 Claims, 12 Drawing Sheets

```
ATG GAC CTC AAG GAA AGC CCC AGT GAG GGC AGC CTG CAA CCT TCT AGC         48
Met Asp Leu Lys Glu Ser Pro Ser Glu Gly Ser Leu Gln Pro Ser Ser
 1                   5                  10                  15

ATC CAG ATC TTT GCC AAC ACC TCC ACC CTC CAT GGC ATC CGC CAC ATC         96
Ile Gln Ile Phe Ala Asn Thr Ser Thr Leu His Gly Ile Arg His Ile
                20                  25                  30

TTC GTG TAT GGG CCG CTG ACC ATC CGG CGT GTG CTG TGG GCA GTG GCC        144
Phe Val Tyr Gly Pro Leu Thr Ile Arg Arg Val Leu Trp Ala Val Ala
            35                  40                  45

TTC GTG GGC TCT CTG GGC CTG CTG GTG GAG AGC TCT GAG AGG GTG           192
Phe Val Gly Ser Leu Gly Leu Leu Val Glu Ser Ser Glu Arg Val
        50                  55                  60

TCC TAC TAC TTC TCC TAC CAG CAT GTC ACT AAG GTG GAC GAA GTG GTG        240
Ser Tyr Tyr Phe Ser Tyr Gln His Val Thr Lys Val Asp Glu Val Val
    65                  70                  75                  80

GCT CAA AGC CTG GTC TTT CCA GCT GTG ACC GTG ACC CTC TGT AAC AAT GGC    288
Ala Gln Ser Leu Val Phe Pro Ala Val Thr Val Thr Leu Cys Asn Asn Gly
                85                  90              *       95

TTC CGG TTC TCC AGG CTC ACC ACC AAC GAC CTG TAC CAT GCT GGG GAG        336
Phe Arg Phe Ser Arg Leu Thr Thr Asn Asp Leu Tyr His Ala Gly Glu
            100                 105                 110
```

Fig. 1A

```
CTG CTG GCC CTG CTG GAT GTC AAC CTG CAG ATC CCG GAC CCC CAT CTG     384
Leu Leu Ala Leu Leu Asp Val Asn Leu Gln Ile Pro Asp Pro His Leu
        115                 120                 125

GCT GAC CCC GTG CTG GAG GCC CTG CGG CAG AAG GCC AAC TTC AAG         432
Ala Asp Pro Val Leu Glu Ala Leu Arg Gln Lys Ala Asn Phe Lys
    130                 135                 140

CAC TAC AAA CCC AAG CAG TTC AGC ATG CTG GAG TTC CTG CAC CGT GTG     480
His Tyr Lys Pro Lys Gln Phe Ser Met Leu Glu Phe Leu His Arg Val
145                 150                 155                 160

GGC CAT GAC CTG AAG GAT ATG ATG CTC TAC TGC AAG TTC AAA GGG CAG     528
Gly His Asp Leu Lys Asp Met Met Leu Tyr Cys Lys Phe Lys Gly Gln
                165                 170                 175
                                     *

GAG TGC GGC CAC CAA GAC TTC ACC ACA GTG TTT ACA AAA TAT GGG AAG     576
Glu Cys Gly His Gln Asp Phe Thr Thr Val Phe Thr Lys Tyr Gly Lys
    *           180                 185                 190

TGT TAC ATG TTT AAC TCA GGA GAT GGC AAA CCT CTG CTC ACC ACG         624
Cys Tyr Met Phe Asn Ser Gly Asp Gly Lys Pro Leu Leu Thr Thr
 *              195                 200                 205

GTC AAG GGG ACA GGC AAC GGG CTG GAG ATC ATG CTG GAC ATT CAG         672
Val Lys Gly Thr Gly Asn Gly Leu Glu Ile Met Leu Asp Ile Gln
210                 215                 220
```

```
CAG GAT GAG TAC CTG CCC ATC TGG GGA GAG ACA GAG ACG ACA TTT       720
Gln Asp Glu Tyr Leu Pro Ile Trp Gly Glu Thr Glu Thr Thr Phe
225                 230                 235                 240

GAA GCA GGA GTG AAA GTT CAG ATC CAC AGT CAG TCT GAG CCA CCT TTC   768
Glu Ala Gly Val Lys Val Gln Ile His Ser Gln Ser Glu Pro Pro Phe
        245                 250                 255

ATC CAA GAG CTG CTT GGC TTT GGG GTG GCT CCA GGG TTC CAG ACC TTT GTG  816
Ile Gln Glu Leu Leu Gly Phe Gly Val Ala Pro Gly Phe Gln Thr Phe Val
            260                 265                 270

GCC ACA CAG CAG AGG CTC ACA TAC CTG CCC CCA CCG TGG GGT GAG       864
Ala Thr Gln Gln Arg Leu Thr Tyr Leu Pro Pro Pro Trp Gly Glu
275                 280                 285

TGC CGA TCC TCA GAG ATG GGC CTC GAC TTT CCT TTT TAC AGC ATC       912
Cys Arg Ser Ser Glu Met Gly Leu Asp Phe Pro Phe Tyr Ser Ile
*       290                 295                 300

ACC GCC TGT AGG ATT GAC TGT GAG ACC CGC TAC ATT GTG GAA AAC TGC   960
Thr Ala Cys Arg Ile Asp Cys Glu Thr Arg Tyr Ile Val Glu Asn Cys
305             *       310                 315                 320 *

AAC TGC CGC ATG GTT CAC ATG CCA GGG GAT GCC CCT TTT TGT ACC CCT   1008
Asn Cys Arg Met Val His Met Pro Gly Asp Ala Pro Phe Cys Thr Pro
*       325                 330                 335         *
```

```
GAG CAG CAC AAG GAG TGT GCA GAG CCT GCC CTA GGT CTG TTG GCG GAA       1056
Glu Gln His Lys Glu Cys Ala Glu Pro Ala Leu Gly Leu Leu Ala Glu
            340             *   345                 350

AAG GAC AGC AAT TAC TGT CTC TGC AGG ACA CCC TGC AAC CTA ACC CGC       1104
Lys Asp Ser Asn Tyr Cys Leu Cys Arg Thr Pro Cys Asn Leu Thr Arg
            355             *   360         * 365

TAC AAC AAA GAG CTC TCC ATG TCC ATG GTG AAG ATC CCC AGC TCA GCC       1152
Tyr Asn Lys Glu Leu Ser Met Ser Met Val Lys Ile Pro Ser Ser Ala
370                 375                 380

AAG TAC CTT GAG AAG AAA TTT AAC AAA TCA GAA TAT ATC TCA GAG           1200
Lys Tyr Leu Glu Lys Lys Phe Asn Lys Ser Glu Tyr Ile Ser Glu
    385                 390                 395             400

AAC ATC CTT GTT CTT GTG CTG GAT ATA TTT TTT GAA GTT GCT CTC AAT       1248
Asn Ile Leu Val Leu Val Leu Asp Ile Phe Phe Glu Val Ala Leu Asn
            405                 410                 415

ATT GAA CAG AAG AAG GCG TAT GAA CAG GTT GCT GCC TTA CTT GGT GAT ATT  1296
Ile Glu Gln Lys Lys Ala Tyr Glu Gln Val Ala Ala Leu Leu Gly Asp Ile
            420                 425                 430

GGT GGT CAG ATG GGA TTG TTC ATT GGT GCT AGT ATC CTT ACA ATA CTA       1344
Gly Gly Gln Met Gly Leu Phe Ile Gly Ala Ser Ile Leu Thr Ile Leu
435                 440                 445
```

*Fig. 1D*

```
GAG CTC TTT GAT TAT ATT TAT GAG CTG ATC AAA GAG AAG CTA TTA GAC    1392
Glu Leu Phe Asp Tyr Ile Tyr Glu Leu Ile Lys Glu Lys Leu Leu Asp
        450                     455                 460

CTG CTT GGC AAA GAG GAG GAA GGG AGC CAC GAT GAG AAT GTG AGT        1440
Leu Leu Gly Lys Glu Glu Glu Gly Ser His Asp Glu Asn Val Ser
465                     470                     475         480

ACT TGT GAC ACA ATG CCA AAC CAC TCT GAA ACC ATC AGT CAC GCT GTG    1488
Thr Cys Asp Thr Met Pro Asn His Ser Glu Thr Ile Ser His Ala Val
                485                     490                 495

AAC GTG CCC CTG CAG ACG ACC CTG GGG ACC TTG GAG ATT GCC TGC        1536
Asn Val Pro Leu Gln Thr Thr Leu Gly Thr Leu Glu Ile Ala Cys
        500                     505                 510

TGA                                                                1539
```

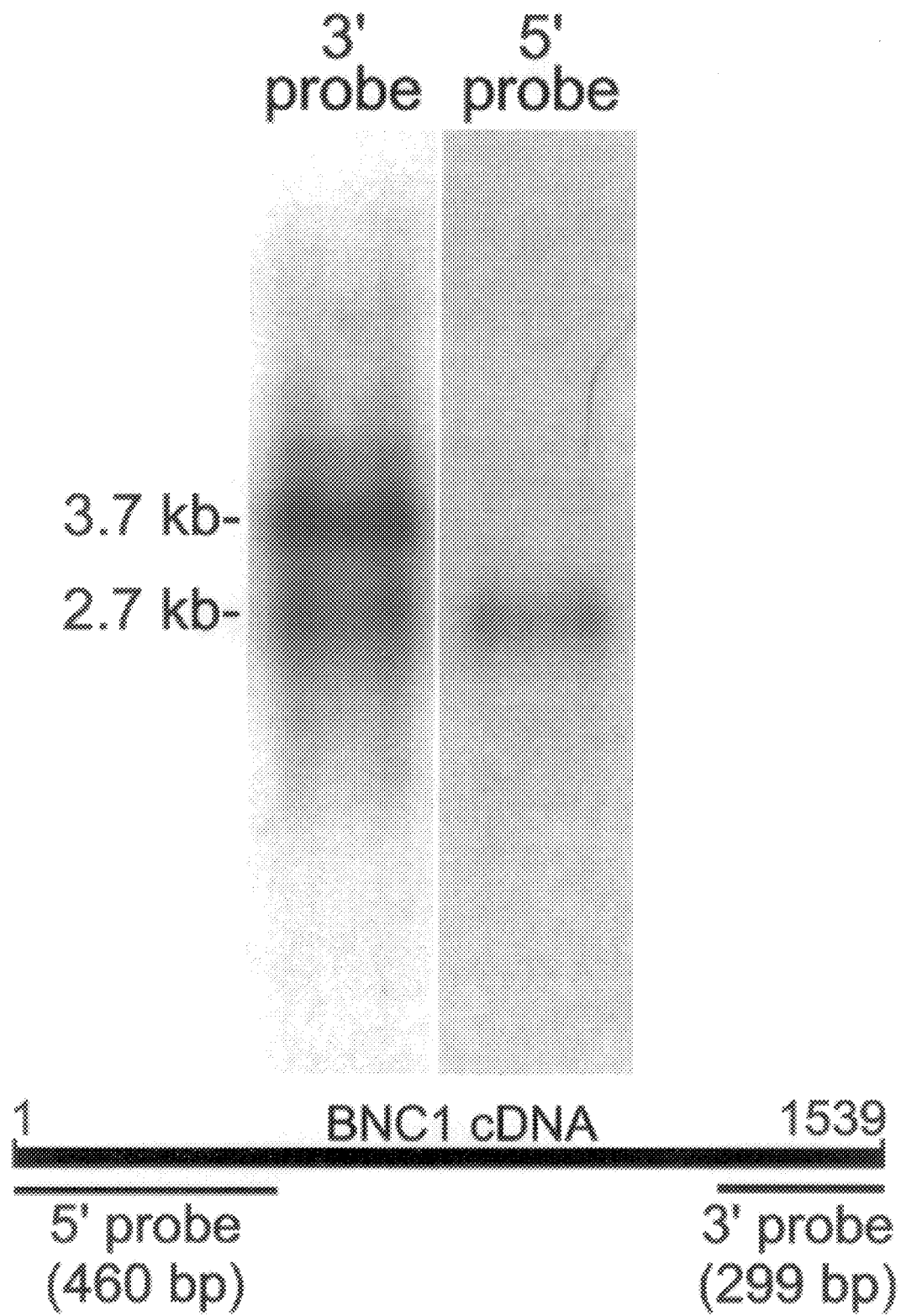

○ Control/Na⁺
● BNC1/K⁺
■ BNC1/Na⁺

5,892,018

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
  ( A ) LENGTH: 1539 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( i x ) FEATURE:
  ( A ) NAME/KEY: CDS
  ( B ) LOCATION: 1..1536

( x i ) SEQUENCE DESCRIPTION: SEQ ID NO:1:

| ATG | GAC | CTC | AAG | GAA | AGC | CCC | AGT | GAG | GGC | AGC | CTG | CAA | CCT | TCT | AGC | 48 |
| Met | Asp | Leu | Lys | Glu | Ser | Pro | Ser | Glu | Gly | Ser | Leu | Gln | Pro | Ser | Ser | |
| 1 | | | | 5 | | | | | 10 | | | | | 15 | | |

| ATC | CAG | ATC | TTT | GCC | AAC | ACC | TCC | ACC | CTC | CAT | GGC | ATC | CGC | CAC | ATC | 96 |
| Ile | Gln | Ile | Phe | Ala | Asn | Thr | Ser | Thr | Leu | His | Gly | Ile | Arg | His | Ile | |
| | | | 20 | | | | | 25 | | | | | 30 | | | |

| TTC | GTG | TAT | GGG | CCG | CTG | ACC | ATC | CGG | CGT | GTG | CTG | TGG | GCA | GTG | GCC | 144 |
| Phe | Val | Tyr | Gly | Pro | Leu | Thr | Ile | Arg | Arg | Val | Leu | Trp | Ala | Val | Ala | |
| | | 35 | | | | | 40 | | | | | 45 | | | | |

| TTC | GTG | GGC | TCT | CTG | GGC | CTG | CTG | CTG | GTG | GAG | AGC | TCT | GAG | AGG | GTG | 192 |
| Phe | Val | Gly | Ser | Leu | Gly | Leu | Leu | Leu | Val | Glu | Ser | Ser | Glu | Arg | Val | |
| | 50 | | | | | 55 | | | | | 60 | | | | | |

| TCC | TAC | TAC | TTC | TCC | TAC | CAG | CAT | GTC | ACT | AAG | GTG | GAC | GAA | GTG | GTG | 240 |
| Ser | Tyr | Tyr | Phe | Ser | Tyr | Gln | His | Val | Thr | Lys | Val | Asp | Glu | Val | Val | |
| 65 | | | | | 70 | | | | | 75 | | | | | 80 | |

| GCT | CAA | AGC | CTG | GTC | TTC | CCA | GCT | GTG | ACC | CTC | TGT | AAC | CTC | AAT | GGC | 288 |
| Ala | Gln | Ser | Leu | Val | Phe | Pro | Ala | Val | Thr | Leu | Cys | Asn | Leu | Asn | Gly | |
| | | | | 85 | | | | | 90 | | | | | 95 | | |

| TTC | CGG | TTC | TCC | AGG | CTC | ACC | ACC | AAC | GAC | CTG | TAC | CAT | GCT | GGG | GAG | 336 |
| Phe | Arg | Phe | Ser | Arg | Leu | Thr | Thr | Asn | Asp | Leu | Tyr | His | Ala | Gly | Glu | |
| | | | 100 | | | | | 105 | | | | | 110 | | | |

| CTG | CTG | GCC | CTG | CTG | GAT | GTC | AAC | CTG | CAG | ATC | CCG | GAC | CCC | CAT | CTG | 384 |
| Leu | Leu | Ala | Leu | Leu | Asp | Val | Asn | Leu | Gln | Ile | Pro | Asp | Pro | His | Leu | |
| | | 115 | | | | | 120 | | | | | 125 | | | | |

| GCT | GAC | CCC | TCC | GTG | CTG | GAG | GCC | CTG | CGG | CAG | AAG | GCC | AAC | TTC | AAG | 432 |
| Ala | Asp | Pro | Ser | Val | Leu | Glu | Ala | Leu | Arg | Gln | Lys | Ala | Asn | Phe | Lys | |
| | 130 | | | | | 135 | | | | | 140 | | | | | |

| CAC | TAC | AAA | CCC | AAG | CAG | TTC | AGC | ATG | CTG | GAG | TTC | CTG | CAC | CGT | GTG | 480 |
| His | Tyr | Lys | Pro | Lys | Gln | Phe | Ser | Met | Leu | Glu | Phe | Leu | His | Arg | Val | |
| 145 | | | | | 150 | | | | | 155 | | | | | 160 | |

| GGC | CAT | GAC | CTG | AAG | GAT | ATG | ATG | CTC | TAC | TGC | AAG | TTC | AAA | GGG | CAG | 528 |
| Gly | His | Asp | Leu | Lys | Asp | Met | Met | Leu | Tyr | Cys | Lys | Phe | Lys | Gly | Gln | |
| | | | | 165 | | | | | 170 | | | | | 175 | | |

| | | | | | | | | | | | | | | | | |
|---|---|---|---|---|---|---|---|---|---|---|---|---|---|---|---|---|
| GAG | TGC | GGC | CAC | CAA | GAC | TTC | ACC | ACA | GTG | TTT | ACA | AAA | TAT | GGG | AAG | 576 |
| Glu | Cys | Gly | His | Gln | Asp | Phe | Thr | Thr | Val | Phe | Thr | Lys | Tyr | Gly | Lys | |
| | | | 180 | | | | 185 | | | | | 190 | | | | |
| TGT | TAC | ATG | TTT | AAC | TCA | GGC | GAG | GAT | GGC | AAA | CCT | CTG | CTC | ACC | ACG | 624 |
| Cys | Tyr | Met | Phe | Asn | Ser | Gly | Glu | Asp | Gly | Lys | Pro | Leu | Leu | Thr | Thr | |
| | | 195 | | | | | 200 | | | | | 205 | | | | |
| GTC | AAG | GGG | GGG | ACA | GGC | AAC | GGG | CTG | GAG | ATC | ATG | CTG | GAC | ATT | CAG | 672 |
| Val | Lys | Gly | Gly | Thr | Gly | Asn | Gly | Leu | Glu | Ile | Met | Leu | Asp | Ile | Gln | |
| | 210 | | | | | 215 | | | | | 220 | | | | | |
| CAG | GAT | GAG | TAC | CTG | CCC | ATC | TGG | GGA | GAG | ACA | GAG | GAA | ACG | ACA | TTT | 720 |
| Gln | Asp | Glu | Tyr | Leu | Pro | Ile | Trp | Gly | Glu | Thr | Glu | Glu | Thr | Thr | Phe | |
| 225 | | | | | 230 | | | | | 235 | | | | | 240 | |
| GAA | GCA | GGA | GTG | AAA | GTT | CAG | ATC | CAC | AGT | CAG | TCT | GAG | CCA | CCT | TTC | 768 |
| Glu | Ala | Gly | Val | Lys | Val | Gln | Ile | His | Ser | Gln | Ser | Glu | Pro | Pro | Phe | |
| | | | | 245 | | | | | 250 | | | | | 255 | | |
| ATC | CAA | GAG | CTG | GGC | TTT | GGG | GTG | GCT | CCA | GGG | TTC | CAG | ACC | TTT | GTG | 816 |
| Ile | Gln | Glu | Leu | Gly | Phe | Gly | Val | Ala | Pro | Gly | Phe | Gln | Thr | Phe | Val | |
| | | | | 260 | | | | | 265 | | | | | 270 | | |
| GCC | ACA | CAG | GAG | CAG | AGG | CTC | ACA | TAC | CTG | CCC | CCA | CCG | TGG | GGT | GAG | 864 |
| Ala | Thr | Gln | Glu | Gln | Arg | Leu | Thr | Tyr | Leu | Pro | Pro | Pro | Trp | Gly | Glu | |
| | | 275 | | | | | 280 | | | | | 285 | | | | |
| TGC | CGA | TCC | TCA | GAG | ATG | GGC | CTC | GAC | TTT | TTT | CCT | GTT | TAC | AGC | ATC | 912 |
| Cys | Arg | Ser | Ser | Glu | Met | Gly | Leu | Asp | Phe | Phe | Pro | Val | Tyr | Ser | Ile | |
| | 290 | | | | | 295 | | | | | 300 | | | | | |
| ACC | GCC | TGT | AGG | ATT | GAC | TGT | GAG | ACC | CGC | TAC | ATT | GTG | GAA | AAC | TGC | 960 |
| Thr | Ala | Cys | Arg | Ile | Asp | Cys | Glu | Thr | Arg | Tyr | Ile | Val | Glu | Asn | Cys | |
| 305 | | | | | 310 | | | | | 315 | | | | | 320 | |
| AAC | TGC | CGC | ATG | GTT | CAC | ATG | CCA | GGG | GAT | GCC | CCT | TTT | TGT | ACC | CCT | 1008 |
| Asn | Cys | Arg | Met | Val | His | Met | Pro | Gly | Asp | Ala | Pro | Phe | Cys | Thr | Pro | |
| | | | | 325 | | | | | 330 | | | | | 335 | | |
| GAG | CAG | CAC | AAG | GAG | TGT | GCA | GAG | CCT | GCC | CTA | GGT | CTG | TTG | GCG | GAA | 1056 |
| Glu | Gln | His | Lys | Glu | Cys | Ala | Glu | Pro | Ala | Leu | Gly | Leu | Leu | Ala | Glu | |
| | | | 340 | | | | | 345 | | | | | 350 | | | |
| AAG | GAC | AGC | AAT | TAC | TGT | CTC | TGC | AGG | ACA | CCC | TGC | AAC | CTA | ACC | CGC | 1104 |
| Lys | Asp | Ser | Asn | Tyr | Cys | Leu | Cys | Arg | Thr | Pro | Cys | Asn | Leu | Thr | Arg | |
| | | 355 | | | | | 360 | | | | | 365 | | | | |
| TAC | AAC | AAA | GAG | CTC | TCC | ATG | GTG | AAG | ATC | CCC | AGC | AAG | ACA | TCA | GCC | 1152 |
| Tyr | Asn | Lys | Glu | Leu | Ser | Met | Val | Lys | Ile | Pro | Ser | Lys | Thr | Ser | Ala | |
| | 370 | | | | | 375 | | | | | 380 | | | | | |
| AAG | TAC | CTT | GAG | AAG | AAA | TTT | AAC | AAA | TCA | GAA | AAA | TAT | ATC | TCA | GAG | 1200 |
| Lys | Tyr | Leu | Glu | Lys | Lys | Phe | Asn | Lys | Ser | Glu | Lys | Tyr | Ile | Ser | Glu | |
| 385 | | | | | 390 | | | | | 395 | | | | | 400 | |
| AAC | ATC | CTT | GTT | CTG | GAT | ATA | TTT | TTT | GAA | GCT | CTC | AAT | TAT | GAG | ACA | 1248 |
| Asn | Ile | Leu | Val | Leu | Asp | Ile | Phe | Phe | Glu | Ala | Leu | Asn | Tyr | Glu | Thr | |
| | | | | 405 | | | | | 410 | | | | | 415 | | |
| ATT | GAA | CAG | AAG | AAG | GCG | TAT | GAA | GTT | GCT | GCC | TTA | CTT | GGT | GAT | ATT | 1296 |
| Ile | Glu | Gln | Lys | Lys | Ala | Tyr | Glu | Val | Ala | Ala | Leu | Leu | Gly | Asp | Ile | |
| | | | 420 | | | | | 425 | | | | | 430 | | | |
| GGT | GGT | CAG | ATG | GGA | TTG | TTC | ATT | GGT | GCT | AGT | ATC | CTT | ACA | ATA | CTA | 1344 |
| Gly | Gly | Gln | Met | Gly | Leu | Phe | Ile | Gly | Ala | Ser | Ile | Leu | Thr | Ile | Leu | |
| | | 435 | | | | | 440 | | | | | 445 | | | | |
| GAG | CTC | TTT | GAT | TAT | ATT | TAT | GAG | CTG | ATC | AAA | GAG | AAG | CTA | TTA | GAC | 1392 |
| Glu | Leu | Phe | Asp | Tyr | Ile | Tyr | Glu | Leu | Ile | Lys | Glu | Lys | Leu | Leu | Asp | |
| | 450 | | | | | 455 | | | | | 460 | | | | | |
| CTG | CTT | GGC | AAA | GAG | GAG | GAC | GAA | GGG | AGC | CAC | GAT | GAG | AAT | GTG | AGT | 1440 |
| Leu | Leu | Gly | Lys | Glu | Glu | Asp | Glu | Gly | Ser | His | Asp | Glu | Asn | Val | Ser | |
| 465 | | | | | 470 | | | | | 475 | | | | | 480 | |
| ACT | TGT | GAC | ACA | ATG | CCA | AAC | CAC | TCT | GAA | ACC | ATC | AGT | CAC | GCT | GTG | 1488 |
| Thr | Cys | Asp | Thr | Met | Pro | Asn | His | Ser | Glu | Thr | Ile | Ser | His | Ala | Val | |
| | | | | 485 | | | | | 490 | | | | | 495 | | |

| | | | | | | | | | | | | | | | | |
|---|---|---|---|---|---|---|---|---|---|---|---|---|---|---|---|---|
| AAC | GTG | CCC | CTG | CAG | ACG | ACC | CTG | GGG | ACC | TTG | GAG | GAG | ATT | GCC | TGC | 1536 |
| Asn | Val | Pro | Leu | Gln | Thr | Thr | Leu | Gly | Thr | Leu | Glu | Glu | Ile | Ala | Cys | |
| | | 500 | | | | | 505 | | | | | 510 | | | | |

TGA  1539

(2) INFORMATION FOR SEQ ID NO:2:

(i) SEQUENCE CHARACTERISTICS:
        (A) LENGTH: 512 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Leu Lys Glu Ser Pro Ser Glu Gly Ser Leu Gln Pro Ser Ser
 1               5                  10                  15

Ile Gln Ile Phe Ala Asn Thr Ser Thr Leu His Gly Ile Arg His Ile
                 20                  25                  30

Phe Val Tyr Gly Pro Leu Thr Ile Arg Arg Val Leu Trp Ala Val Ala
             35                  40                  45

Phe Val Gly Ser Leu Gly Leu Leu Val Glu Ser Ser Glu Arg Val
         50                  55                  60

Ser Tyr Tyr Phe Ser Tyr Gln His Val Thr Lys Val Asp Glu Val Val
 65                  70                  75                  80

Ala Gln Ser Leu Val Phe Pro Ala Val Thr Leu Cys Asn Leu Asn Gly
                     85                  90                  95

Phe Arg Phe Ser Arg Leu Thr Thr Asn Asp Leu Tyr His Ala Gly Glu
                100                 105                 110

Leu Leu Ala Leu Leu Asp Val Asn Leu Gln Ile Pro Asp Pro His Leu
                115                 120                 125

Ala Asp Pro Ser Val Leu Glu Ala Leu Arg Gln Lys Ala Asn Phe Lys
        130                 135                 140

His Tyr Lys Pro Lys Gln Phe Ser Met Leu Glu Phe Leu His Arg Val
145                 150                 155                 160

Gly His Asp Leu Lys Asp Met Met Leu Tyr Cys Lys Phe Lys Gly Gln
                    165                 170                 175

Glu Cys Gly His Gln Asp Phe Thr Thr Val Phe Thr Lys Tyr Gly Lys
                180                 185                 190

Cys Tyr Met Phe Asn Ser Gly Glu Asp Gly Lys Pro Leu Leu Thr Thr
        195                 200                 205

Val Lys Gly Gly Thr Gly Asn Gly Leu Glu Ile Met Leu Asp Ile Gln
    210                 215                 220

Gln Asp Glu Tyr Leu Pro Ile Trp Gly Glu Thr Glu Glu Thr Thr Phe
225                 230                 235                 240

Glu Ala Gly Val Lys Val Gln Ile His Ser Gln Ser Glu Pro Pro Phe
                    245                 250                 255

Ile Gln Glu Leu Gly Phe Gly Val Ala Pro Gly Phe Gln Thr Phe Val
                260                 265                 270

Ala Thr Gln Glu Gln Arg Leu Thr Tyr Leu Pro Pro Pro Trp Gly Glu
            275                 280                 285

Cys Arg Ser Ser Glu Met Gly Leu Asp Phe Phe Pro Val Tyr Ser Ile
        290                 295                 300

Thr Ala Cys Arg Ile Asp Cys Glu Thr Arg Tyr Ile Val Glu Asn Cys
305                 310                 315                 320

Asn Cys Arg Met Val His Met Pro Gly Asp Ala Pro Phe Cys Thr Pro
                    325                 330                 335
```

| | | | | | | | | | | | | | | |
|---|---|---|---|---|---|---|---|---|---|---|---|---|---|---|
| Glu | Gln | His | Lys<br>340 | Glu | Cys | Ala | Glu | Pro<br>345 | Ala | Leu | Gly | Leu<br>350 | Leu | Ala | Glu |
| Lys | Asp | Ser<br>355 | Asn | Tyr | Cys | Leu | Cys<br>360 | Arg | Thr | Pro | Cys<br>365 | Asn | Leu | Thr | Arg |
| Tyr | Asn<br>370 | Lys | Glu | Leu | Ser | Met<br>375 | Val | Lys | Ile | Pro | Ser<br>380 | Lys | Thr | Ser | Ala |
| Lys<br>385 | Tyr | Leu | Glu | Lys | Lys<br>390 | Phe | Asn | Lys | Ser | Glu<br>395 | Lys | Tyr | Ile | Ser | Glu<br>400 |
| Asn | Ile | Leu | Val | Leu<br>405 | Asp | Ile | Phe | Phe | Glu<br>410 | Ala | Leu | Asn | Tyr | Glu<br>415 | Thr |
| Ile | Glu | Gln | Lys<br>420 | Lys | Ala | Tyr | Glu | Val<br>425 | Ala | Ala | Leu | Leu | Gly<br>430 | Asp | Ile |
| Gly | Gly | Gln | Met<br>435 | Gly | Leu | Phe | Ile<br>440 | Gly | Ala | Ser | Ile | Leu<br>445 | Thr | Ile | Leu |
| Glu | Leu<br>450 | Phe | Asp | Tyr | Ile | Tyr<br>455 | Glu | Leu | Ile | Lys | Glu<br>460 | Lys | Leu | Leu | Asp |
| Leu<br>465 | Leu | Gly | Lys | Glu | Glu<br>470 | Asp | Glu | Gly | Ser | His<br>475 | Asp | Glu | Asn | Val | Ser<br>480 |
| Thr | Cys | Asp | Thr | Met<br>485 | Pro | Asn | His | Ser | Glu<br>490 | Thr | Ile | Ser | His<br>495 | Ala | Val |
| Asn | Val | Pro | Leu<br>500 | Gln | Thr | Thr | Leu | Gly<br>505 | Thr | Leu | Glu | Glu | Ile<br>510 | Ala | Cys |

(2) INFORMATION FOR SEQ ID NO:3:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Phe Met Arg Phe
1

(2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Phe Leu Phe Gln Pro Gln Arg Phe
1                5

(2) INFORMATION FOR SEQ ID NO:5:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Ala Gly Glu Gly Leu Ser Ser Pro Phe Trp Ser Leu Ala Ala Pro Gln

-continued

```
1               5                    1 0                       1 5
Arg Phe
```

DNA SEQUENCES ENCODING A BRAIN SODIUM CHANNEL PROTEIN

CROSS REFERENCE TO RELATED APPLICATION

This application is a continuation of Provisional application 60/072,104 which was filed Apr. 2, 1996 and entitled NOVEL BRAIN SODIUM CHANNEL PROTEIN FAMILY AND DNA SEQUENCES ENCODING SAME.

FIELD OF THE INVENTION

The present invention relates generally to sodium channel proteins and more particularly to sodium channel proteins located in the mammalian brain, to DNA sequences encoding sodium channel proteins, to the polypeptide products of recombinant expression of these DNA sequences, to peptides whose sequences are based on amino acid sequences deduced from these DNA sequences, and to procedures relating to the development of drugs that influence function of such proteins.

BACKGROUND OF THE INVENTION

Ion channels in mammalian systems have been, and currently are, the subject of intensive scientific investigation because of the importance and variety of their biochemical functions. Ion channels are now understood to be polypeptide or protein structures with tertiary-quaternary structure forming interior pores embedded in cell membrane walls, that control the flow of ionic currents.

There are many types of ion channels which share both similarity of function and amino acid sequence, thus defining familial relationships between many of these channels. Current work shows there are ion channel families comprised of voltage gated sodium, potassium, and calcium channels, as well as the ligand gated acetylcholine receptors, glycine receptors, and gamma aminobutyric acid receptors.

A great deal is known about voltage gated sodium channels. These are transmembrane proteins responsible for the early sodium permeability increase underlying initial depolarization of the action potential in many excitable cells such as muscle, nerve, and cardiac cells. However knowledge of non-voltage gated sodium channels that are involved in either determining resting membrane potential in the brain or in responding to neurotransmitters is virtually nonexistent.

This is despite the fact that several brain diseases have been associated with channel abnormalities and central nervous system dysfunction. Psychiatric diseases including depression and schizophrenia, and dementias, such as Alzheimer's all have association with dysfunction of the central nervous system whose neurons are controlled and regulated by sodium channels.

Considerably more work has been accomplished with voltage dependent sodium channels. The molecular characteristics of these channels has proven quite complex with multiple isoforms, differential tissue expression and limited sequence conservation between the various families of proteins.

Recent studies have identified a new family of Na+ channels whose characteristic features include Na+ selectivity, inhibition by amiloride, and a conserved primary structure (Chalfie, M., (1990) *Nature* 345, 410–416; Driscol, M., (1991) *Nature* 349, 588–593; Huang, M., (1994) *Nature* 367, 467–470; Canessa, C. M., (1993) *Nature* 361, 467–470; Canessa, C. M., (1994) *Nature* 367, 463–467; McDonald, F. J., (1994) *Am. J. Physiol.* 266, L728-L734; McDonald, F. J., (1995) *Am. J. Physiol.* 268, C1157–C1163; Voilley, N., (1994) *Proc. Natl. Acad. Sci. U.S.A.* 91, 247–251; Lingueglia, E. (1993) *FEBS Lett.* 318, 95–99; Waldmann, R. (1995) *J. Biol Chem.* 270, 27411–27414; Lingueglia, E. (1995) *Nature* 378, 730–733). Family members contain 500 to 800 residues. Sequence analysis and studies of topology suggest that the amino and carboxyl termini are intracellular, that there are two hydrophobic regions that traverse the membrane (M1 and M2), and that between M1 and M2 there lies a large cysteine-rich extracellular domain (Snyder, P. M. (1994) *J. Biol. Chem.* 269, 24379≅24383; Renard, S. (1994) *J. Biol. Chem.* 269, 12981–12986; Canessa, C. M. (1994) *Am. J. Physiol.* 267, C1682–C1690).

The best characterized members of this family are the amiloride-sensitive epithelial Na+ channels (ENaC) that control Na+ and fluid absorption in the kidney, colon, and lung. ENaC channels are constructed from at least three homologous subunits ($\alpha$-, $\beta$-, and $\gamma$ENaC) (Canessa, C. M., (1993) *Nature* 361, 467–470; Canessa, C. M., (1994) *Nature* 367, 463–467; McDonald, F. J., (1994) *Am. J. Physiol.* 266, L728–L734; McDonald, F. J., (1995) *Am. J. Physiol.* 268, C1157–C1163; Voilley, N., (1994) *Proc. Natl. Acad. Sci. U.S.A.* 91, 247–251; Lingueglia, E. (1993) *FEBS Lett.* :318, 95–99). Mutations in this channel cause a hereditary form of hypertension called Liddle's syndrome (Shimkets, R. A., (1994) *Cell* 79, 407–414) and pseudohypoaldosteronism (Chang, S. S., (1996) *Nature Genetics* 12, 248–253). These channels may also be involved in detection of salty taste (Li, X. J. (1994) *Proc. Natl. Acad. Sci. U.S.A.* 91, 1814–1818). A closely related subunit, $\delta$NaCh, is expressed in pancreas, testis, ovary, and brain. $\delta$ NaCh generates Na+channels when coexpressed with $\beta$- and $\gamma$ENaC (Waldmann, R. (1995) *J. Biol Chem.* 270, 27411–27414), suggesting that it may be part of the ENaC subfamily of channels. Several family members have also been discovered in *C. elegans*, including MEC-4, MEC-10, and DEG-1, which when mutated produce a touch-insensitive phenotype (Chalfie, M., (1990) *Nature* 345, 410–416; Driscol, M., (1991) *Nature* 349, 588–593; Huang, M., (1994) *Nature* 367, 467–470). Specific mutations in the C-elegans group cause neural degeneration (Chalfie, M., (1990) *Nature* 345, 410–416; Driscol, M., (1991) *Nature* 349, 588–593). Based on this ability to produce cell degeneration, family members in *C. elegans* are called "degenerins." The most recent addition to this family is a Phe-Met-Arg-Phe-NH$_2$ (FMRF-amide)-stimulated Na+ channel (FaNaCh) cloned from *Helix* (Lingueglia, E. (1995) *Nature* 378, 730–733).

As can be seen from the foregoing a continuing need exits in the art for further identification and characterization of sodium channel proteins to genetically link diseases to mutations in this gene, to identify disease-causing mutations in the gene, for uses as a diagnostic tool to screen populations for a predisposition to brain diseases, to assay for new ligands and antagonists for the channel, to treat brain disease or the enhance brain function, to use for gene therapy protocols for treatment of brain disease, and to further identify and characterize still other novel and closely related members of this subfamily of sodium channels.

SUMMARY OF THE INVENTION

According to the invention a novel cDNA from human brain has been cloned which encodes upon expression a non-voltage-dependent Na+ channel. This protein has some features in common with a channel family that includes subunits of the mammalian epithelial Na+ channel, the *Caenorhabditis elegans* degenerins, and the *Helix aspersa*

FMRF-amidegated Na+ channel. Like other family members it is inhibited by amiloride. However, its predicted structure differs from other family members, its discrimination between Na+ and Li+ is different, and in contrast to other mammalian family members, coexpression with other cloned subunits of the family does not increase current. The protein has a unique pattern of expression with transcripts detected only in adult human brain and in spinal cord. Thus, it is the first cloned member of a new subfamily of mammalian Na+ channels.

The protein is termed BNC1 for Brain Na' Channel, and 1 with the expectation that additional subunits are contemplated within the scope of the invention.

As used herein the term "nucleotide sequence" shall include DNA as well as RNA and shall include alternate DNA(RNA) forms such as genomic DNA, mRNA and DNA (RNA) prepared by partial or total chemical synthesis from nucleotides as well as DNA(RNA) with deletions or mutations.

The term "protein" as used herein shall include all peptides and proteins (recombinant, synthetic or purified from natural sources), which are capable of functioning as amiloride sensitive nonvoltage dependent sodium channels as determined by the assays disclosed herein and shall include all such peptide fragments and synthetic fragments assembled to be duplicative of such proteins.

DESCRIPTION OF THE FIGURES

FIGS. 1(A)–(E) depict the nucleotide SEQ ID NO:1 and amino acid sequence SEQ ID NO:2 of the BNC1 open reading frame. Underlined sequence refers to predicted hydrophobic, membrane spanning segments. Conserved cysteines are indicated with asterisks. Potential glycosylation sites in the extracellular domain are indicated with squares. Potential protein kinase C phosphorylation site in the intracellular domain is indicated with a circle.

FIGS. 4A and 4B, 4A is a Northern blot analysis of BNC1 expression in adult human tissue. 4B is a Northern blot analysis of BNC1 expression in specific regions of the adult human brain. Each lane contains approximately 2 $\mu$g of poly(A)$^+$ RNA; the amount of RNA in each lane was adjusted to observe identical levels of β actin expression. Filters were hybridized with a probe corresponding to the coding sequence of BNC1 as described under the Examples section. Blots were exposed to film for 4 days; a 7-day exposure of 4B showed that both transcripts were evident to some extent in every lane.

FIG. 5 depicts Northern blot analysis of human brain RNA using 5' and 3' specific BNC1 probes. 5 $\mu$g of adult human brain poly(A)+RNA were run on a 1.2% agarose-formaldehyde gel, transferred to nitrocellulose filter, and hybridized with labeled probes prepared from either the 5' or 3' ends of the BNC1 cDNA as shown at the bottom.

DETAILED DESCRIPTION OF THE INVENTION

Figure 2:
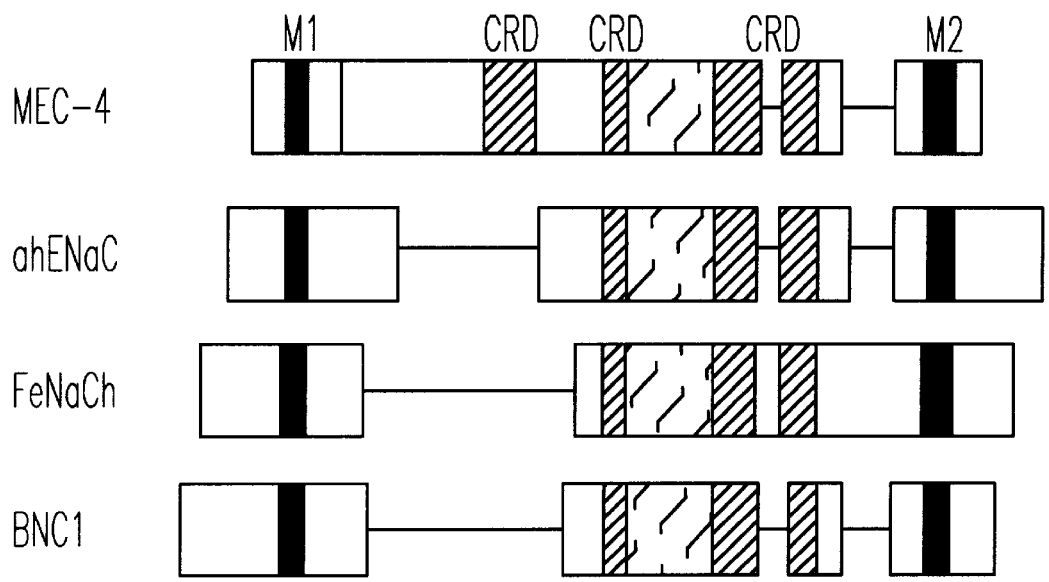
FIG. 2 is a structural comparison of cloned family members. MEC-4 and αhENaC were chosen as representative members of the degenerin and ENaC/δ NaCh proteins respectively. Black areas identify transmembrane segments (M1 and M2) shaded areas indicate cysteine-rich domains (CRD), cross hatched area indicates additional region of conserved sequence, and thin black line indicates regions which are missing in some family members.

The present invention provides novel purified and isolated nucleic acid sequences encoding human brain sodium channel protein. In presently preferred forms, the DNA sequences comprise cDNA sequences encoding a novel, nonvoltage dependent human brain sodium channel protein. Specifically, the sequence isolated is depicted in SEQ ID NO:1. Alternate DNA forms such as genomic DNA, and DNA prepared by partial or total chemical synthesis from nucleotides as well as DNA with deletions or mutations, is also within the contemplated scope of the invention. Further the sequence information disclosed can be used to generate probes of 15 or more consecutive nucleotides which can be used to isolate the corresponding cDNA as further described herein and as exemplified in the examples.

Association of DNA sequences provided by the invention with homologous or heterologous species expression control DNA sequences such as promoters, operators, regulators, and the like, allows in vivo and in vitro transcription from mRNA which, in turn, is susceptible to translation to provide the novel sodium channel proteins of the invention, and related poly- and oligo-peptides in large quantities. In a presently preferred DNA expression system of the invention sodium channel encoding DNA is operatively linked to a regulatory promoter DNA sequence allowing for in vitro transcription and translation of the protein. In a preferred expression system, cDNA species are injected directly into *Xenopus oocytes* thereby allowing for in vitro translation forming a functional sodium channel capable of demonstrating functional characteristics of native sodium channels including ion selectivity, gating-kinetics, ligand preferences, and sensitivity to pharmacological agents such as TTX for a model assay which mimics in vivo characteristics. This is important for treatment of brain diseases such as psychiatric disease including depression and schizophrenia, and dementias, such as Alzheimer's all of which have been associated with dysfunction of the central nervous system. These assays can be used to identify agonists and antagonists of the channel and such drugs would be of value for treatment of diseases involving neuronal abnormalities. Alternatively, such agents could be used for treatment of diseases with increased or decreased sodium channel activity or neuronal cell membrane depolarization or hyperpolarization, including anxiety, hyperactivity, autism, dyslexia, insomnia, seizures, and the sequela of strokes.

Incorporation of DNA sequences into prokaryotic and eucaryotic host cells by standard transformation and transfection processes, potentially involving suitable viral and circular DNA plasmid vectors, is also within the contemplation of the invention and is expected to provide useful proteins in quantities heretofore unavailable from natural sources. Use of mammalian host cells is expected to provide for such post-translational modifications (e.g. truncation, glycosylation, and tyrosine, serine, or threonine phosphorylation) as may be needed to confer optimal biological activity on recombinant expression products of the invention as more fully set forth hereinafter.

Most of the techniques which are used to transform cells, construct vectors, extract messenger RNA, prepare cDNA libraries, and the like are widely practiced in the art, and most practitioners are familiar with the standard resource materials which describe specific conditions and procedures. However, for convenience, the following paragraphs may serve as a guideline.

Hosts and Control Sequences

Both prokaryotic and eucaryotic systems may be used to express BNC1 encoding sequences; prokaryotic hosts are, of course, the most convenient for cloning procedures. Prokaryotes most frequently are represented by various strains of *E. coli;* however, other microbial strains may also be used. Plasmid vectors which contain replication sites, selectable markers and control sequences derived from a species compatible with the host are used; for example, *E. coli* is typically transformed using derivatives of pBR322, a plasmid derived from an *E. coli* species by Bolivar, et al, *Gene* (1977) 2:95. pBR322 contains genes for ampicillin and tetracycline resistance, and thus provides multiple selectable markers which can be either retained or destroyed in constructing the desired vector. Commonly used prokaryotic control sequences which are defined herein to include promoters for transcription initiation, optionally with an operator, along with ribosome binding site sequences, include such commonly used promoters as the beta-lactase (penicillinase) and lactose (lac) promoter systems (Chang, et al, *Nature* (1977) 198:1056) and the tryptophan (trp) promoter system (Goeddel, et al, *Nucleic Acids Res* (1980) 8:4057) and the lambda derived $P_L$ promoter and N-gene ribosome binding site (Shimatake, et al, *Nature* (1981) 292:128).

In addition to bacteria, eucaryotic microbes, such as yeast, may also be used as hosts. Laboratory strains of *Saccharomyces cerevisiae,* Baker's yeast, are most used although a number of other strains or species are commonly available. Vectors employing, for example, the $2\mu$ origin of replication of Broach, J. R., *Meth Enz* (1983) 101:307, or other yeast compatible origins of replication (see, for example, Stinchcomb, et al, *Nature* (1979) 282:39, Tschumper, G., et al, *Gene* (1980) 10:157 and Clarke, L, et al, *Meth Enx* (1983) 101:300) may be used. Control sequences for yeast vectors include promoters for the synthesis of glycolytic enzymes (Hess, et al, *J Adv Enzyme Reg* (1968) 7:149; Holland, et al, *Biochemistry* (1978) 17:4900). Additional promoters known in the art include the promoter for 3-phosphoglycerate kinase (Hitzeman, et al *J Biol Chem* (1980) 255:2073). Other promoters, which have the additional advantage of transcription controlled by growth conditions and/or genetic background are the promoter regions for alcohol dehydrogenase 2, isocytochrome C, acid phosphatase, degradative enzymes associated with nitrogen metabolism, the alpha factor system and enzymes responsible for maltose and galactose utilization. It is also believed terminator sequences are desirable at the 3' end of the coding sequences. Such terminators are found in the 3' untranslated region following the coding sequences in yeast-derived genes.

It is a so, of course, possible to express genes encoding polypeptides in eucaryotic host cell cultures derived from multicellular organisms. See, for example, Axel, et al, U.S. Pat. No. 4,399,216. These systems have the additional advantage of the ability to splice out introns and thus can be used directly to express genomic fragments. Useful host cell lines include VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers, et al, *Nature* (1978) 273:113), or other viral promoters such as those derived from polyoma, Adenovirus 2, bovine papilloma virus, or avian sarcoma viruses. The controllable promoter, hMTII (Karin, M., et al, *Nature* (1982) 299:797–802) may also be used. General aspects of mammalian cell host system transformations have been described by Axel (supra). It now appears, also that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eucaryotes.

Transformations

Depending on the host cell used, transformation is done using standard techniques appropriate to such cells. The calcium treatment employing calcium chloride, as described by Cohen, S. N., *Proc Natl Acad Sci* (USA) 1972) 69:2110, or the rbCl2 method described in Maniatis, et al, *Molecular Cloning: A Laboratory Manual* (1982) Cold Spring Harbor Press, p. 254 and Hanahan, D., *J Mol Biol* (1983) 166:557–580 may be used for prokaryotes or other cells which contain substantial cell wall barriers. For mammalian cells without such cell walls, the calcium phosphate precipitation method of Graham and van der Eb, *Virology* (1978) 52:546, optionally as modified by Wigler, M., et al, *Cell* (1979) 16:777–785 may be used. Transformations into yeast may be carried out according to the method of Beggs, J. D. *Nature* (1978) 275:104–109 or of Hinnen, A., et al, *Proc Natl Acad Sci* (USA) (1978) 75:1929.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

The DNA sequences which form the vectors are available from a number of sources. Backbone vectors and control systems are generally found on available "host" vectors which are used for the bulk of the sequences in construction. Typical sequences have been set forth above. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleoside derivatives. The entire gene sequence for genes of sizable length, e.g., 500–1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., *Nature*

(1981) 292:756; Nambair, K. P., et al, *Science* (1984) 223:1299; Jay, Ernest, *J Biol Chem* (1984) 259:6311.

Synthetic oligonucleotides are prepared by either the phosphotriester method as described by Edge, et al, *Nature* (supra) and Duckworth, et al, *Nucleic Acids Res* (1981) 9:1691 or the phosphoramidite method as described by Beaucage, S. L., and Caruthers, M. H., *Tet Letts* (1981) 22:1859 and Matteucci, M. D., and Caruthers, M. H., *J Am Chem Soc* (1981) 103:3185 and can be prepared using commercially available automated oligonucleotide synthesizers. Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1–2 mM ATP, 1.7 y pmoles $\gamma$32P-ATP (2.9 mCi/mmole), 0.1 mM spermidine, 0.1 mM EDTA.

Once the components of the desired vectors are thus available, they can be excised and ligated using standard restriction and ligation procedures.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 $\mu$g of plasmid or DNA sequence is cleaved by one unit of enzyme in about 20 $\mu$l of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6mM MgCl2, 6 mM DTT and 0.1–1.0 mM dNTPs. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture is extracted with phenol/chloroform and ethanol precipitated. Treatment under appropriate conditions with S1 nuclease or BAL-31 results in hydrolysis of any single-stranded portion.

Ligations are performed in 15–50 $\mu$l volumes under the following standard conditions and temperatures: for example, 20 mM Tris-Cl pH 7.5, 10 mM $MgCl_2$, 10 mM DTT, 33 $\mu$g/ml BSA, 10 mM-50 mM NaCl, and either 40 $\mu$M ATP, 0.01–0.02 (Weiss) units T4 DNA ligase at 0 C (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 $\mu$g/ml total DNA concentrations (5–100 nM total end concentration). Intermolecular blunt end ligations are performed at 1 $\mu$M total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent self-ligation of the vector. Digestions are conducted at pH 8 in approximately 10 mM Tris-HCl, 1 mM EDTA using about 1 unit of BAP or CIP per $\mu$g of vector at 600 for about one hour. In order to recover the nucleic acid fragments, the preparation is extracted with phenol/chloroform and ethanol precipitated. Alternatively, religation can be prevented in vectors which have been double digested by additional restriction enzyme digestion and separation of the unwanted fragments.

For portions of vectors derived from cDNA or genomic DNA which require sequence modifications, site specific primer directed mutagenesis may be used (Zoller, M. J., and Smith, M. *Nucleic Acids Res* (1982) 10:64837–6500 and Adelman, J. P., et al, DNA (1983) 2:183–193). This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting partially or fully double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are washed after hybridization with kinased synthetic primer at a wash temperature which permits binding of an exact match, but at which the mismatches with the original strand are sufficient to prevent binding. Plaques which hybridize with the probe are then picked, cultured, and the DNA recovered.

Verification of Construction

Correct, ligations for plasmid construction can be confirmed by first transforming *E. coli* strain MC1061 obtained from Dr. M. Casadaban (Casadaban, M., et al, *J Mol Biol* (1980) 138:179–207) or other suitable host with the ligation mixture. Successful transformants are selected by ampicilin, tetracycline or other antibiotic resistance by using other markers depending on the mode of plasmid construction, as is understood in the art. Plasmids from the transformants are then prepared according to the method of Clewell, D. B., et al, *Proc Natl Acad Sci (USA)* (1969) 62:1159, optionally following chloramphenicol amplification (Clewell, D. B., *J Bacteriol* (1972) 110:667). Several mini DNA preps are commonly used, e.g., Holmes, D. S., et al, *Anal Biochem Acids Res* (1979) 7:1513–1523. The isolated DNA is analyzed by restriction and/or sequenced by the dideoxy nucleotide method of Sanger, F., et al, *Proc Natl Acad Sci* (USA) (1977) 74:5463 as further described by Messing, et al, *Nucleic Acids Res* (1981) 9:309, o4 by the method of Maxam, et al, *Methods in Enzymology* (1980) 65:499.

Hosts Exemplified

Host strains used in cloning and prokaryotic expression herein are as follows:

For cloning and sequencing, and for expression of construction under control of most bacterial promoters, *E. coli* strains such as MC1061, DH1, RR1, C600hf1, K803, HB101, JA221, and JM101 can be used.

The proteins of the present invention may also be produced by chemical synthesis such as solid phase peptide synthesis, using known amino acid sequences or amino acid sequences derived from the DNA sequence of the genes of interest. Such methods are known to those skilled in the art. Chemical synthesis of peptides may be preferable if a small fragment of the antigen in question is capable of raising an immunological response in the subject of interest.

The novel protein products of the invention include polypeptides with the primary structural conformation (i.e. amino acid sequence) of sodium channel proteins as set froth in FIG. 1 and SEQ ID NO:2, as well as peptide fragments thereof and synthetic peptides assembled to be duplicative of amino acid sequences thereof. Proteins, protein fragments and synthetic proteins or peptides of the invention are projected to have uses earlier described including therapeutic, diagnostic, and prognostic assays and protocols and will provide the basis for monoclonal and polyclonal antibodies specifically reactive with the channel protein.

Thus as set forth herein the invention includes the provision of a novel subfamily of non-voltage dependent mammalian brain sodium channel proteins as exemplified by the novel DNA sequences set for the in FIG. 1 (SEQ ID NO:1), as well as DNA sequences which hybridize thereto under hybridization conditions of the stringency equal to or greater than the conditions of the stringency employed in the initial isolation of cDNAs of the invention, and DNA sequences encoding the same allelic variant or analog sodium channel protein through use of at least in part degenerate codons. The sequences can also be used to located and identify other closely related members of this sub family as described in Cannessa, et al (1994) *Nature* 367, 463–467 incorporated herein by reference.

The following examples are intended to further illustrate the invention and are not intended to limit the scope of the invention in any way. All references cited herein, whether previously or in the following examples, are expressly incorporated in their entirety by reference.

EXAMPLES

Abbreviations used herein includes the following: M1 and M2, first and second membrane spanning sequences, respectively; ENaC, epithelial Na+ channel with α, β, and γ subunits; δNaCh, δ subunit of Na+ channel; FMR-amide, Phe-Met-Arg-Phe-Nh$_2$ (SEQ ID NO:3); FaNaCh, FMRF-amide-gated Na+ channel; F-8-F-amide, Phe-Leu-Phe-Gln-Pro-Gln-Arg-Phe-Nh$_2$ (SEQ ID NO:4); A-18-F-amide, Ala-Gly-Glu-Gly-Leu-Ser-Ser-Pro-Phe-Trp-Ser-Leu-Ala-Ala-Pro-Gln-Arg-Phe-Nh2 (SEQ ID NO:5); RACE, rapid amplification of cDNA ends; EST, expressed sequence tag; PCR, polymerase chain reaction; bp, base pair(s); kb, kilobase(s).

Cloning—A complete BNC1 cDNA was obtained by extending an expressed sequence tag (GenBank™ accession number Z45660) in the 5' direction using rapid amplification of cDNA ends (RACE) technique according to the protocol provided with the Marathon cDNA Amplification Kit from Clontech. Human brain cDNA which had been tagged with an adapter primer at the 5' end (Clontech) was used as template in 5' RACE reactions. In brief, the tagged cDNA was used in a PCR reaction with a sense primer corresponding to the tag sequence and a gene-specific antisense primer corresponding to nucleotides 256–282 of the EST sequence. The 3' end of the gene-specific primer spanned the 3' end of the cDNA and contained a sequence complementary to the stop codon. RACE PCR reactions were done using reagents in the Advantage cDNA PCR core kit (Clontech) which contains a combination of Klentaq-1 and Deep Vent DNA polymerases and TagStart antibody. Thermal cycling was done in a Perkin Elmer DNA Thermal Cycler using a program of one cycle at 94° C. for 1 minute; 5 cycles of 94° C. for 30 seconds and 72° C. for 4 minutes; 5 cycles of 94° C. for 30 seconds and 70° C. for 4 minutes; then 20–25 cycles of 94° C. for 20 seconds and 68° C. for 4 minutes. PCR products were purified on an agarose gel using β-agarase from New England Biolabs, cloned into the pCR$^{II}$ vector (Invitrogen), and sequenced. DNA sequencing was done on an Applied Biosystems automated Sequencer using fluorescent dye-labeled terminators. An 1809-bp fragment was obtained from the 5' RACE reaction which contained 270 nucleotides of upstream untranslated sequence and a 1539-bp open reading frame extending to the 3' stop codon. This fragment was digested in its entirety out of the pCR$^{II}$ vector as a Not/I/KpnI fragment and ligated into the compatible sites of the pMT3 vector for expression in oocytes. Oligonucleotides were prepared on an automated Applied Biosystems oligonucleotide synthesizer. Relationship of proteins in the phylogenetic tree was derived using the Pileup alignment program from Genetics Computer Group (GCG). The diagram was generated using the Distances program (GCG) with Kimura substitution, followed by the Growtree program with the UPGMA option.

Northern Blot Analysis—Northern blots contained 2 μg of poly(a)+RNA isolated from specific adult human tissues or from sections of the brain (Clontech). Probes were prepared by random prime labeling (Pharmacia Biotech Inc.). PCR primers specific for the 5' and 3' ends of the protein coding sequence of the BNC1 cDNA were used in a PCR reaction to generate a fragment containing the entire coding sequence of BNC1. This fragment was cloned into the pCR$^{II}$ vector and used to probe the multiple tissue blots. An EcoRI/SphI 460-bp fragment was isolated from the 5' end of the coding region clone and used as a 5' end specific probe. A 299-bp PCR product corresponding to the 3' end of the coding region of BNC1 was cloned for use as a 3' end specific probe. Filters were hybridized overnight at 42° C. in a buffer containing 50% formamide, 5 X SSPE, 2% SDS, 10 X Denhardt's solution, and 100 μg/ml salmon sperm DNA. Filters were washed with 0.1 X SSC, 0.1% SDS at 55° C. and exposed to Kodak X-Omat AR film for 4 days at −70° C.

Expression of BNC1 in *Xenopus laevis* Oocytes—BNC1 was expressed in *Xenopus oocytes* by nuclear injection of BNC1 cDNA cloned into pMT3 (0.2–0.3 ng). Control oocytes were injected with H$_2$O. α-, β-, and γhENaC (αβγhENaC) were expressed as described previously. Oocytes were maintained at 18° C. in modified Barth's solution, and current was measured by two-electrode voltage clamp 1 day after injection. During voltage clamp, oocytes were bathed in 116 mM NaCl, 2 mM KCl, 0.4 mM CaCl$_2$, 1 mM Mg Cl$_2$, 5 mM Hepes (pH 7.4 with NaOH). To determine ionic selectivity, NaCl was replaced with LiCl or KCl. Current-voltage relationships were determined by stepping from a holding potential of −60 mV to potentials between −100 and +40 mV for 1 second. Amiloride-sensitive current was obtained by subtracting current during exposure to a maximal concentration of amiloride (100 μM) from current prior to amiloride addition. Phe-Met-Arg-Phe-NH$_2$ (FMRF-am-ide), Phe-Leu-Phe-Gln-Pro-Gln-Arg-Phe-NH$_2$ (F-8-F-amide), and Ala-Gly-Glu-Gly-Leu-Ser-Ser-Pro-Phe-Trp-Ser-Leu-Ala-Ala-Pro-Gln-Arg-Phe-NH$_2$ (A-18-F-amide) were obtained from Sigma and were added to the bathing solution at 1–30 μM.

Cloning and Sequence Analysis—To identify new mammalian Na+ channels, the BLAST sequence alignment tags (EST) was used with the amino acid sequences of hENaC and the degenerins. A 299-nucleotide sequence (GenBank TM number Z45660) obtained from human brain cDNA was found. The EST was capable of encoding a 94-amino acid open reading frame. Using methods described above, an 1809-bp cDNA containing a 1539-bp open reading frame with stops in all three reading frames upstream of the putative start methionine was found (FIG. 1 shows the deduced amino acid sequence of BNC1).

FIG. 2 shows that BNC1 has a predicted structure with some features similar to that of other cloned amiloride-sensitive Na+ channels and the degenerins. Of particular interest are the two hydrophobic transmembrane segments and the extracellular cysteine-rich domains. There is also an area with limited sequence conservation between two Cysteine-rich domains (cross-hatch area in FIG. 2). However, there are also significant differences between BNC1 and other cloned members of the family (FIG. 2). In the amino-terminal half of the extracellular domain, BNC1 seems more similar to FaNaCh because it lacks sequences found in degenerins and ENaC. Yet, in the carboxyl-terminal half of the extracellular domain, BNC1 is more similar in length to ENaC and the degenerins than to FaNaCh. BNC1 has a relatively short carboxyl-terminal intracellular tail. It lacks the conserved proline-rich sequences of ENaC that may be involved in protein-protein interactions. It also lacks the PPPXYXXL motif which determines the amount of cell surface protein and which is deleted from βhENaC or γ hENaC in patients with Liddle's syndrome. BNC1 has consensus N-linked glycosylation sequences in the extracellular domain (FIG. 1). The amino-terminal intracellular sequence contains one consensus sequence for protein kinase C phosphorylation.

Figure 3:
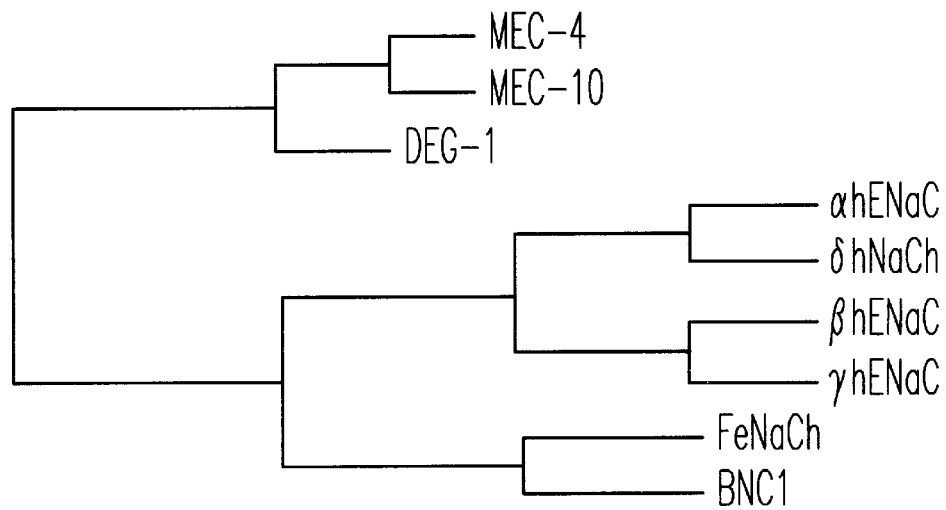
FIG. 3 is a phylogenetic tree of family members.

Although absolute homology is relatively low, BNC1 shares slightly greater overall amino acid sequence identity with FaNaCh than with other members of the family. BNC1 is 28.4% identical with FaNaCh, 24.2–26.6% identical with α-, β-, and γENaC and δNaCh, and 24.4–25.4% identical with the degenerins. Despite the species difference, phylogenetic analysis placed BNC1 closest to FaNaCh, rather than to other mammalian members of the family (FIG. 3).

Figure 4A:
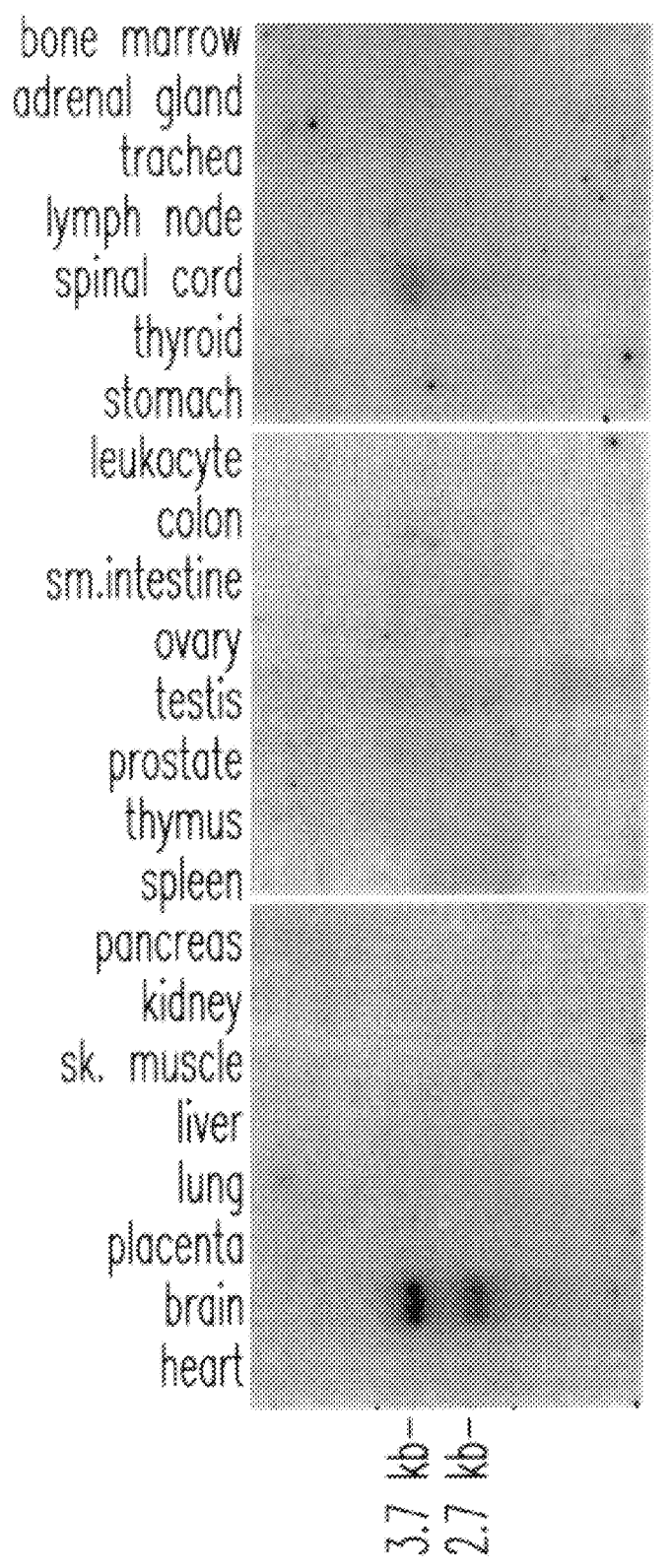
Figure 4B:
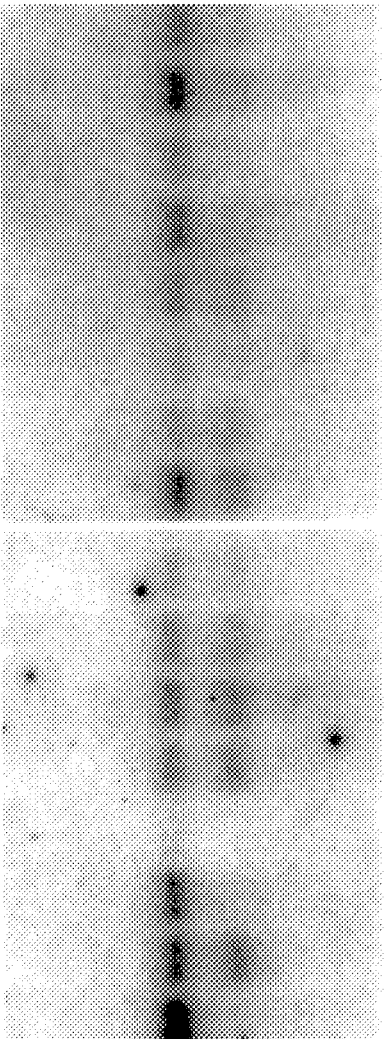

Northern Blot Analysis -Northern blot analysis was used to examine the transcription pattern in BNC1. 4A shows that transcripts were detected in human brain and spinal cord, but not in a number of other tissues. The two BNC1 transcripts were expressed to some extent in every region of the adult human brain that was analyzed (FIG. 4B). The greatest relative abundance appeared to be in cerebellum, cerebral cortex, medulla, amygdala, and subthalamic nucleus.

The expression pattern of BNC1 is unique; expression primarily in the central nervous system contrasts with previously identified mammalian members of the family. Although transcripts of α- and γENaC and δNaCh have been detected in brain, they are much more prevalent in other tissues. α- and γENaC are most abundant in epithelia of kidney, colon, and lung, and 6NaCh is most abundant in testis, ovary, and pancreas. Expression of nonmammalian members of the family has been reported in excitable tissue. Transcription of FaNaCh occurs in muscle and nervous tissue of Helix, and the degenerins are expressed in the peripheral and central nervous system of *C. elegans.*

When the entire coding region of BNC1 was used as a probe, two transcripts were detected, 2.7 and 3.7 kb in length (FIG. 4, A and B). In general, relative hybridization to the two transcripts was similar in most brain regions, although there was a greater relative abundance of the large transcript in the cerebellum, medulla, spinal cord, corpus collosum, pypothalamus, substantia nigra, and thalamus. To investigate the relationship between the two transcripts, we prepared probes from the 5' and 3' regions of BNC1 cDNA (corresponding to the amino and carboxyl termini of the predicted protein) and hybridized them to a Northern blot containing human brain poly(A)+ RNA (FIG. 5). Whereas the 3' probe hybridized with both transcripts, the 5' probe hybridized with the 2.7-kb transcript only. These data indicate that the cDNA reported here is produced by the small transcript. There are at least two possible explanations for the presence of two transcripts. First, alternative splicing at the amino terminus might generate two transcripts from a single gene. Second, there may be two genes with very similar sequences corresponding to the 3' end of BNC1. Further investigation is necessary to distinguish between these alternatives. In either case, the data suggest the possibility of structural and thus functional complexity with multimeric channel proteins.

Figure 6:
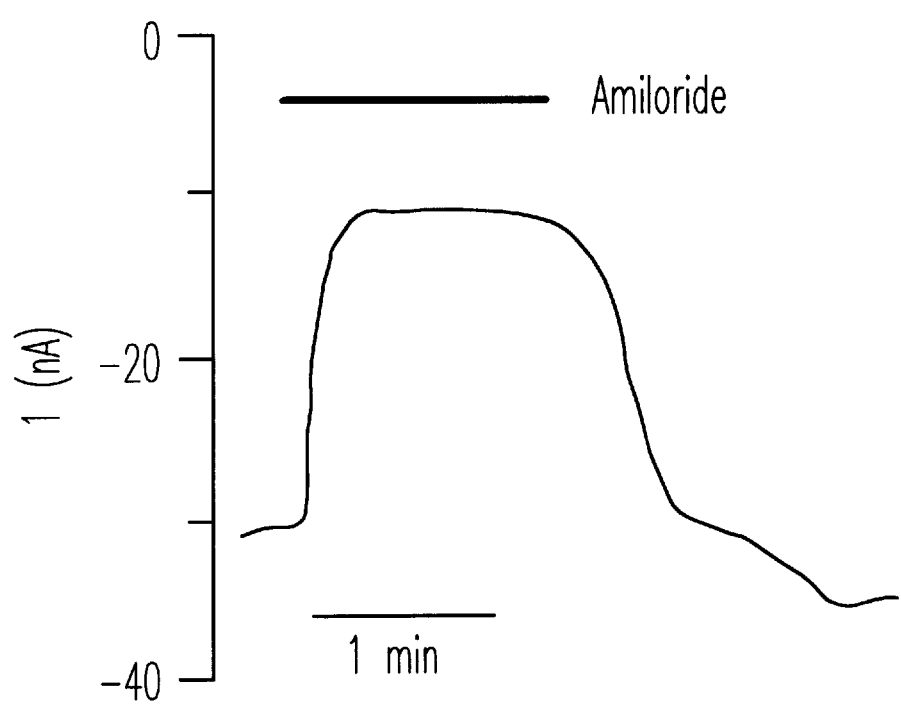
FIG. 6 is a representative current trace depicting expression of BNC1 in *Xenopus oocytes*. Oocytes were injected with cDNA encoding BNC1, and current was measured by a two-electrode voltage clamp, one day after injection at a holding potential of −60 mV. Amiloride (100$\mu$M) was present during the time period indicated by the bar.
Figure 7:
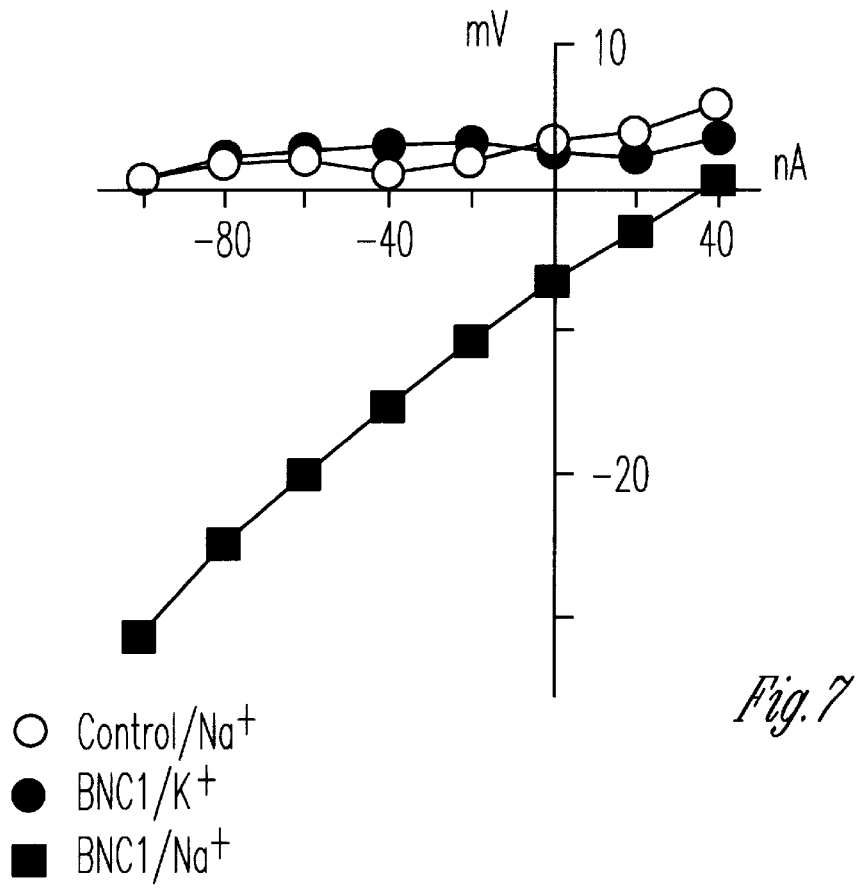
FIG. 7 is a graph depicting current-voltage relationships for amiloride-sensitive current from representative oocytes expressing BNC1 or injected which H$_2$O (Control). Oocyties were bathed in Na+ or K+ containing solution, as indicated.
Figure 8:
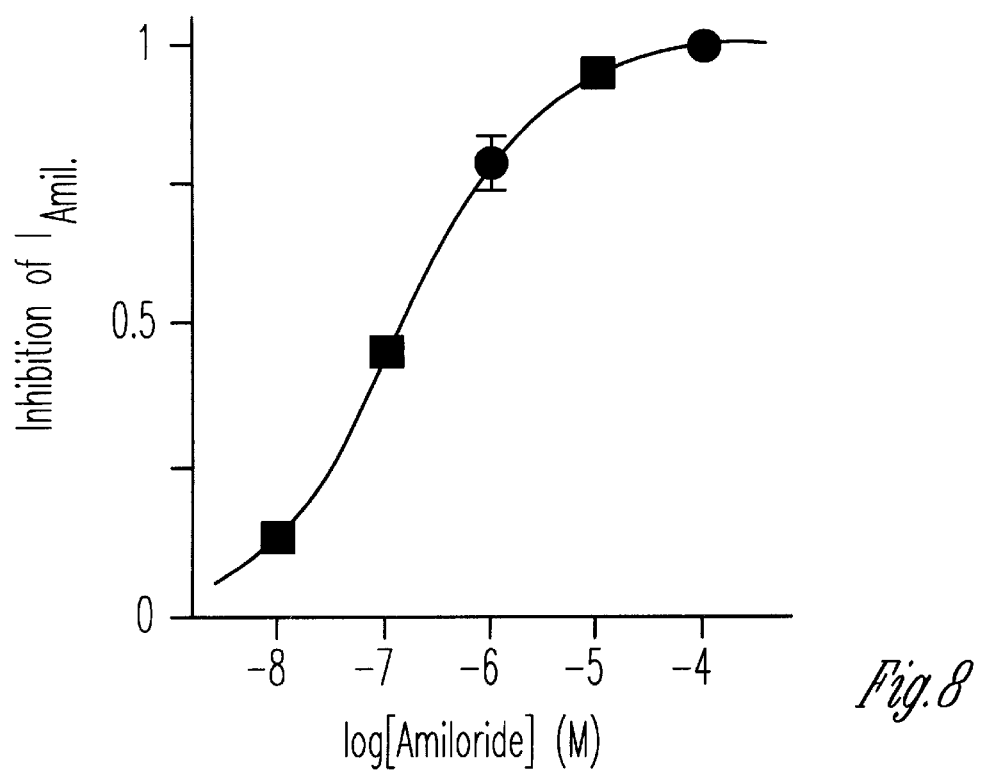
FIG. 8 is a graph depicting the effect of increasing concentrations of amiloride on BNC1 expression, plotted as fraction of response to 100 $\mu$ M amiloride (n=4).

Expression of BNC1 in *Xenopus Oocytes*—Because of its homology with ENaC and FaNaCh Na+ channels, the hypothesis that BNC1 is a Na+ channel was tested. Expression of BNC1 in *Xenopus oocytes* generated a small inward current (holding potential −60 mV) that: was reversibly inhibited by amiloride (14.0±2.7 nA, n=12. FIG. 6). There was no amiloride-sensitive current in control ($H_2O$-injected) oocytes (FIG. 7). The BNC1 current was highly selective for Na+ relative to K+; the reversal potential was 35±6 mV (n=6) in NaCl bathing solution, and the amiloride-sensitive current was abolished by replacing Na+ with K+ in the bathing solution (FIG. 7). The Na+ current was inhibited by amiloride with half-maximal inhibition at 147±23 nM (FIG. 8).

Figure 9:
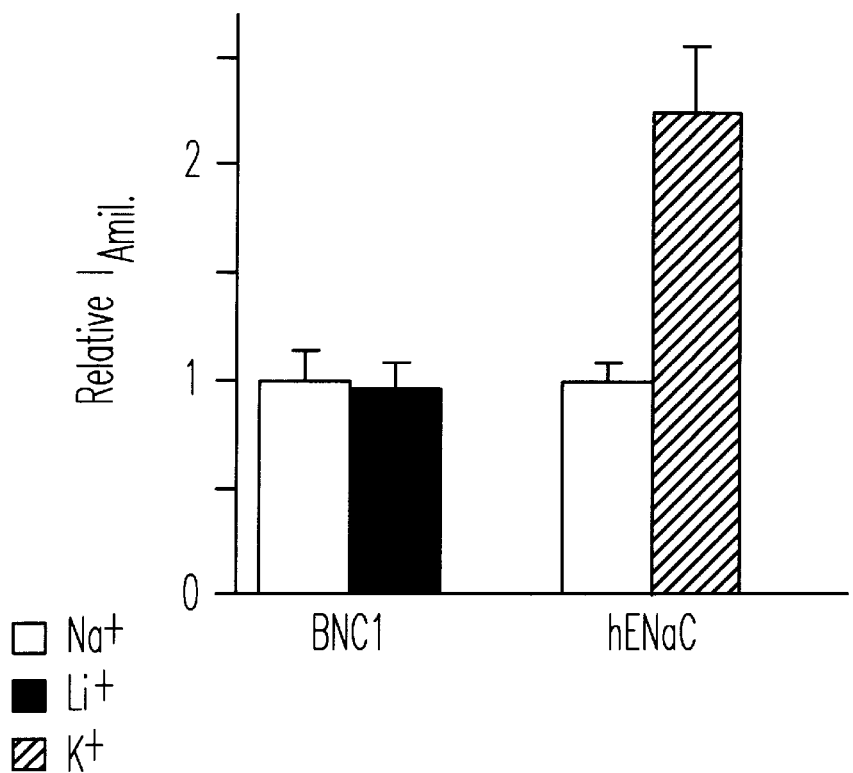
FIG. 9 depicts amiloride-sensitive current measured in presence of Na$^+$, Li$^+$, or K$^+$ as indicated. Data are plotted relative to current in NaCl. Oocyties expressed BNC1 (n=9) or αβγhENaC ("hENaC," n=4) as indicted.

When Na+ was replaced with Li+, equal currents through BNC1 channels were obtained (FIG. 9). This differs from αβγENaC and αENaC which are 2-fold more conductive to Li+ than to Na+ (FIG. 9), and from FaNaCh and δNaCh which are more conductive to Na+ than to Li+. It was previously shown that $Ser^{589}$ in αrENaC was important for Na+/Li+ selectivity; mutation to Ile increased Na+ conductance relative to Li+. The analogous residue in BNC1 and δNaCh) is alanine ($Ala^{442}$), suggesting that this residue might help determine relative Na+/Li+ conductivity in BNC1 as well as in other family members.

Figure 10:
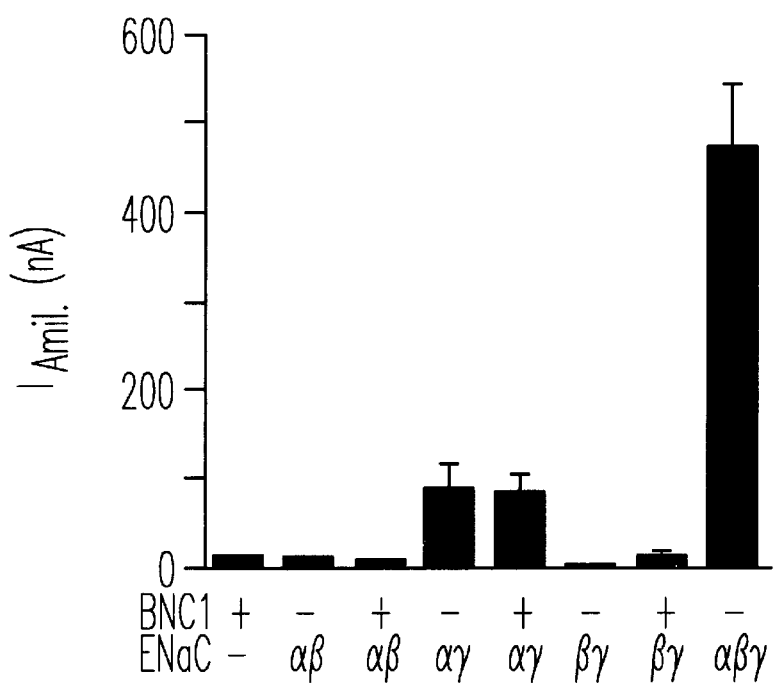
FIG. 10 depicts amiloride-sensitive current in oocyte expressing ENaC subunits with or without BNC1, as indicated. n=5–16 for each except αβγ hENaC where n=3.

Na+ current generated by BNC1 was not significantly increased by coexpression with combinations of α-, β-, and/or γhENaC subunits (FIG. 10). In contrast, coexpression of the three ENaC subunits significantly increased current compared with expression of only two subunits. Thus BNC1 functions as a novel member of the Na+ channel family. The data with BNC1 also contrast with δNaCh in which coexpression with β- and γhENaC markedly increased current.

BNC1 current was postulated to be stimulated by an agonist, much as FaNaCh requires activation by the *Helix aspersa* neuropeptide FMRF-amide. However, BNC1 was not activated by FMRF-amide or the related mammalian peptides F-8-F-amide or A-18-F-amide. Although this suggests that BNC1 is not the mammalian homologue of the Helix FaNaCh, it does not exclude the possibility that BNC1 could be a receptor for another neurotransmitter.

BNC is a novel member of the ENaC/degenerin family. However, it has several significant differences from other cloned members of the family: it has a different predicted structure; it does not discriminate between Na+ and Li+ as current carriers; expression was detected only in the central nervous system; and BNC1 current is not augmented when it is coexpressed with subunits of ENaC. These considerations suggest that BNC1 may be the first cloned member of a new subfamily of mammalian Na+ channels. Although expression of BNC1 generated a Na+ current, the magnitude was small. Ligand-regulated activity rather than constitutive activity would be more consistent with neuronal expression, because constitutive non-voltage-dependent Na+ channel activity could depolarize the cell, thereby disrupting signal transduction, or it could cause toxicity. The large cysteine-rich extracellular domain of BNC1 could have a receptor function. Certainly the large size and presence of multiple cysteine residues is reminiscent of other receptor proteins.

As can be seen from the foregoing the invention accomplished at least all of its objectives.

What is claimed is:

1. A purified and isolated nucleotide sequence which encodes a novel human brain sodium channel protein, said channel protein being characterized by the following:
   (a) non voltage dependent,
   (b) amiloride sensitive,
   (c) nondiscriminate between sodium and lithium current; and said nucleotide sequence being capable of hybridizing to SEQ ID NO:1 under the following conditions:
   1) hybridization at 42° C. in buffer comprising 50% formamide, 5X SSPE, 2% SDS, 10X Denhardt's solution and 100 µg/ml salmon sperm DNA; and
   2) washing at 55° C. in buffer comprising 0.1X SSC and 0.1% SDS.

2. The nucleotide sequence of claim 1 wherein said sequence is SEQ ID NO:1.

3. An expression construct comprising:
   a nucleotides sequence according to claim 1, operatively linked to a regulatory region capable of directing the expression of a human brain nonvoltage dependent sodium channel in a suitable expression host.

4. A vector capable of transforming or transfecting a host cell, said vector comprising an expression construct according to claim 2.

5. The vector of claim 4 wherein said vector is a plasmid based vector.

6. The vector of claim 4 wherein said vector is a viral based vector.

7. The vector of claim 6 wherein said vector is selected from the group consisting of a retroviral vector, a adenoviral vector and a herpes viral vector.

8. A prokaryotic or eucaryotic host cell transformed or transfected with a vector according to claim 4.

9. The host cell of claim 8 wherein said cell is a mammalian cell.

10. The host cell of claim 8 wherein said cell is a *Xenopus oocyte*.

11. An isolated DNA that encodes the following amino acid sequence for a nonvoltage dependent amiloride sensitive brain sodium channel protein of SEQ ID NO:2 or fragments thereof at least 15 nucleotides in length.

12. An isolated cDNA that comprises the following DNA sequence and encodes a nonvoltage dependent brain sodium channel protein; SEQ ID NO:1 or fragments thereof that are at least 15 nucleotides in length.

* * * * *